US00PP24372P2

(12) United States Plant Patent
Ochiai

(10) Patent No.: US PP24,372 P2
(45) Date of Patent: Apr. 1, 2014

(54) ***PERICALLIS* PLANT NAMED 'OCHKEIPILA'**

(50) Latin Name: *Pericallis cruenta*
Varietal Denomination: Ochkeipila

(76) Inventor: Shigeaki Ochiai, Gose (JP)

( * ) Notice: Subject to any disclaimer, the term of this patent is extended or adjusted under 35 U.S.C. 154(b) by 85 days.

(21) Appl. No.: 13/506,815

(22) Filed: May 17, 2012

(51) Int. Cl.
*A01H 5/00* (2006.01)

(52) U.S. Cl.
USPC ..... Plt./480; Plt./263.1

(58) Field of Classification Search
USPC ..... Plt./263.1, 480
See application file for complete search history.

*Primary Examiner* — Susan McCormick Ewoldt
(74) *Attorney, Agent, or Firm* — C. A. Whealy

(57) ABSTRACT

A new and distinct cultivar of *Pericallis* plant named 'Ochkeipila', characterized by its upright and mounded plant habit; freely branching growth habit; freely flowering habit; and daisy-type inflorescences with pink-colored ray florets and red purple-colored disc florets.

1 Drawing Sheet

Botanical designation: *Pericallis cruenta.*
Cultivar denomination: 'OCHKEIPILA'.

BACKGROUND OF THE INVENTION

The present invention relates to a new and distinct cultivar of *Pericallis* plant, botanically known as *Pericallis cruenta* and hereinafter referred to by the name 'Ochkeipila'.

The new *Pericallis* plant is a product of a planned breeding program conducted by the Inventor in Gose City, Nara, Japan. The objective of the breeding program is to create new compact *Pericallis* plants with attractive pink-colored flowers.

The new *Pericallis* plant originated from a cross-pollination made by the Inventor in July, 2006 in Gose City, Nara, Japan of a proprietary selection of *Pericallis cruenta* identified as code number FC1-002, not patented, as the female, or seed, parent with a proprietary selection of *Pericallis cruenta* identified as code number FNP3-005, not patented, as the male, or pollen, parent. The new *Pericallis* plant was discovered and selected by the Inventor as a single flowering plant from within the progeny of the stated cross-pollination in a controlled greenhouse environment in Gose City, Nara, Japan in June, 2010.

Asexual reproduction of the new *Pericallis* plant by terminal cuttings in a controlled greenhouse environment in Gose City, Nara, Japan since June, 2010 has shown that the unique features of this new *Pericallis* plant are stable and reproduced true to type in successive generations.

SUMMARY OF THE INVENTION

Plants of the new *Pericallis* have not been observed under all possible environmental conditions and cultural practices. The phenotype may vary somewhat with variations in environment such as temperature and light intensity, without, however, any variance in genotype.

The following traits have been repeatedly observed and are determined to be the unique characteristics of 'Ochkeipila'. These characteristics in combination distinguish 'Ochkeipila' as a new and distinct cultivar of *Pericallis* plant:

1. Upright and mounded plant habit.
2. Freely branching growth habit.

3. Freely flowering habit.
4. Daisy-type inflorescences with pink-colored ray florets and red purple-colored disc florets.

Plants of the new *Pericallis* differ from plants of the female parent selection primarily in plant habit as plants of the new *Pericallis* are more compact than plants of the female parent selection.

Plants of the new *Pericallis* differ from plants of the male parent selection primarily in ray floret color as plants of the male parent selection have red-colored ray florets.

Plants of the new *Pericallis* can be compared to plants of *Senecio cruentus*×*Pericallis heritieri* 'Sunsenere', disclosed in U.S. Plant Pat. No. 12,162. In side-by-side comparisons conducted in Gose City, Nara, Japan, plants of the new *Pericallis* differed from plants of 'Sunsenere' in the following characteristics:

1. Plants of the new *Pericallis* were more compact than plants of 'Sunsenere'.
2. Plants of the new *Pericallis* had smaller and darker green-colored leaves than plants of 'Sunsenere'.
3. Plants of the new *Pericallis* and 'Sunsenere' differed in ray floret color as plants of 'Sunsenere' had purple-colored florets.

BRIEF DESCRIPTION OF THE PHOTOGRAPH

The accompanying photograph illustrates the overall appearance of the new *Pericallis* plant showing the colors as true as it is reasonably possible to obtain in colored reproductions of this type. Colors in the photograph may differ slightly from the color values cited in the detailed botanical description which accurately describe the colors of the new *Pericallis* plant. The photograph comprises a side perspective view of a typical flowering plant of 'Ochkeipila' grown in a container.

DETAILED BOTANICAL DESCRIPTION

The aforementioned photograph, following observations and measurements describe plants grown in 12-cm containers during the summer in a glass-covered greenhouse in Rheinberg, Germany and under environmental conditions and cultural practices which approximate those generally used in commercial *Pericallis* production. During the production of the plants, day and night temperatures averaged 18° C. and light levels averaged 4,500 lux. Measurements and numerical values represent averages for typical flowering plants. Plants were pinched one time and were 20 weeks old when the photograph and description were taken. In the following description, color references are made to The Royal Horticultural Society Colour Chart, Fourth Edition, 1995, except where general terms of ordinary dictionary significance are used.

Botanical classification: *Pericallis cruenta* 'Ochkeipila'.

Parentage:

*Female, or seed, parent*.—Proprietary selection of *Pericallis cruenta*. identified as code number FC1-002, not patented.

*Male, or pollen, parent*.—Proprietary selection of *Pericallis cruenta* identified as code number FNP3-005, not patented.

Propagation:

*Type*.—Terminal vegetative cuttings.

*Time to initiate roots, summer*.—About five days at 20° C.

*Time to initiate roots, winter*.—About seven days at 20° C.

*Time to produce a rooted young plant, summer*.—About three weeks at 20° C.

*Time to produce a rooted young plant, winter*.—About four weeks at 20° C.

*Root description*.—Fine, fibrous; white in color.

*Rooting habit*.—Freely branching.

Plant description:

*Plant form and growth habit*.—Upright and mounded plant habit; daisy-type inflorescences positioned above the foliar plane; freely branching habit with about nine to eleven lateral branches developing per plant; moderately vigorous growth habit.

*Plant height*.—About 17 cm.

*Plant diameter*.—About 21 cm.

*Lateral branches*.—Length: About 11.5 cm. Diameter: About 2 mm. Internode length: About 3.2 cm. Strength: Strong. Texture: Slightly pubescent. Color: Close to 144A to 144B.

*Foliage description*.—Arrangement: Alternate, simple. Length: About 4.6 cm. Width: About 6.5 cm. Shape: Palmate. Apex: Acute. Base: Cordate. Margin: Palmately lobed; crenate. Texture, upper and lower surfaces: Pubescent. Venation pattern: Pinnate; reticulate. Color: Developing leaves, upper surface: Close to 146A. Developing leaves, lower surface: Close to 147D. Fully expanded leaves, upper surface: Close to 147A; venation, close to 143C. Fully expanded leaves, lower surface: Close to 147D; venation, close to 144B. Petioles: Length: About 3.5 cm. Diameter: About 2 mm. Texture, upper and lower surfaces: Pubescent. Color, upper surface: Close to 145B. Color, lower surface: Close to 145A.

Inflorescence description:

*Appearance*.—Daisy-type inflorescences with oblong-shaped ray florets; inflorescences arising from upper leaf axils and positioned above the foliar plane; disc and ray florets developing acropetally on a capitulum; inflorescences face mostly upright; freely flowering habit with about 55 inflorescences developing per plant.

*Fragrance*.—None detected.

*Natural flowering season*.—In Japan, plants of the new *Pericallis* flower continuously during the spring; plants begin flowering about six weeks after planting.

*Inflorescence longevity*.—Inflorescences last about one week on the plant; inflorescences not persistent.

*Inflorescence buds*.—Height: About 1.2 mm. Diameter: About 0.8 mm. Shape: Ovoid. Color: Close to 144A and 69A.

*Inflorescence size*.—Diameter: About 4.4 cm. Depth (height): About 2.2 cm. Disc diameter: About 1 cm. Receptacle height: About 6.6 mm. Receptacle diameter: About 2 mm.

*Ray florets*.—Shape: Oblong. Length: About 1.75 cm. Width: About 5.6 mm. Apex: Rounded. Base: Obtuse. Margin: Entire. Texture, upper and lower surfaces: Smooth, glabrous. Number of ray florets per inflorescence: About 17 arranged in a single whorl. Color: When opening, upper surface: Close to 68A and 62A. When opening, lower surface: Close to 65A and 87D. Fully opened, upper surface: Close to 65B and 69B; color does not fade with development. Fully opened, lower surface: Close to 69C; color becoming closer to 69D with development.

*Disc florets*.—Shape: Tubular; apex dentate, five-pointed. Length: About 9 mm. Diameter: About 1.5 mm. Number of disc floret per inflorescence: About 142. Color, immature and mature: Close to 72D.

*Phyllaries*.—Quantity per inflorescence: About 20 arranged in a single whorl. Length: About 1.2 cm. Width: About 3 mm. Shape: Ensiform. Apex: Acute. Base: Attenuate. Margin: Entire. Texture, upper and lower surfaces: Smooth, glabrous. Color, upper surface: Close to 144A. Color, lower surface: Close to 144A to 144B.

*Peduncles*.—Length, terminal peduncle: About 3 cm. Length, fourth peduncle: About 6 cm. Length, seventh peduncle: About 8 cm. Diameter: About 2 mm. Strength: Strong. Aspect: Mostly upright. Texture: Smooth, glabrous. Color: Close to 144A.

*Reproductive organs*.—Androecium: Present on disc florets only. Filament length: About 0.5 mm. Filament color: Close to 144B. Anther length: About 1 mm. Anther shape: Rounded. Anther color: Close to 81A. Pollen amount: Scarce. Pollen color: Close to 15A. Gynoecium: Present on both ray and disc florets. Pistil length: About 1 cm. Style length: About 3 mm. Style color: Close to 145C. Stigma shape: Decurrent. Stigma color: Close to 73B. Ovary color: Close to 144C.

*Seeds and fruits*.—Seed and fruit development has not been observed on plants of the new *Pericallis*.

Disease & pest resistance: Plants of the new *Pericallis* have not been observed to be resistant to pathogens and pests common to *Pericallis*.

Temperature tolerance: Plants of the new *Pericallis* have been observed to tolerate temperatures ranging from about 5° C. to about 40° C.

It is claimed:

1. A new and distinct *Pericallis* plant named 'Ochkeipila' as illustrated and described.

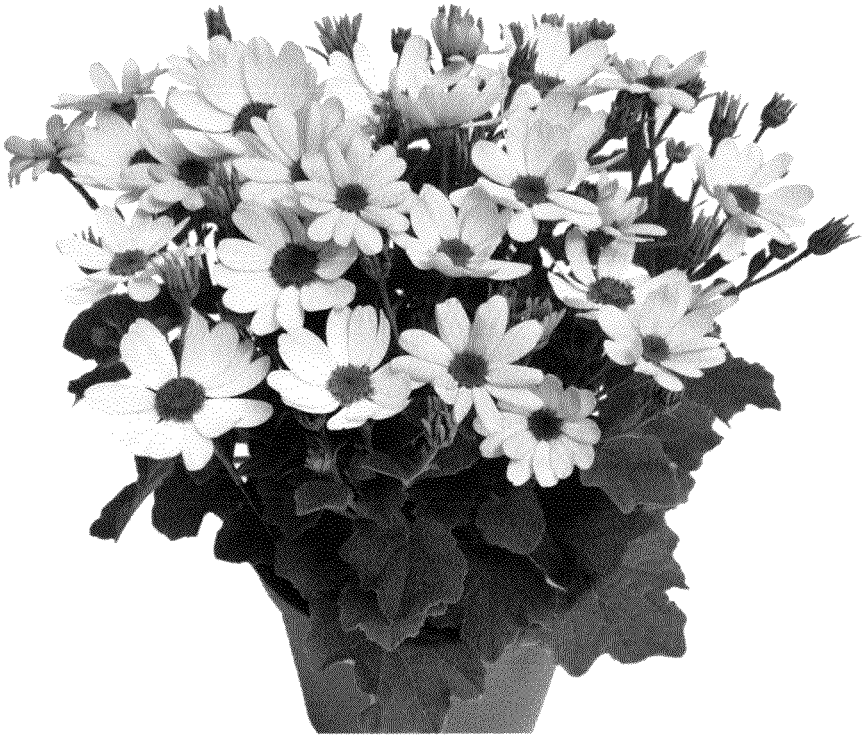

* * * * *